(12) United States Patent
Matarasso

(10) Patent No.: US 7,562,659 B2
(45) Date of Patent: Jul. 21, 2009

(54) RESPIRATORY AID APPARATUS AND METHOD

(76) Inventor: Hasdi Matarasso, 12 Amnon Ve'atmar Street, Netanya (IL) 42202

( * ) Notice: Subject to any disclaimer, the term of this patent is extended or adjusted under 35 U.S.C. 154(b) by 488 days.

(21) Appl. No.: 10/522,073

(22) PCT Filed: Jul. 22, 2003

(86) PCT No.: PCT/IL03/00599

§ 371 (c)(1),
(2), (4) Date: Jul. 6, 2005

(87) PCT Pub. No.: WO2004/009169

PCT Pub. Date: Jan. 29, 2004

(65) Prior Publication Data

US 2006/0011198 A1    Jan. 19, 2006

Related U.S. Application Data

(60) Provisional application No. 60/397,042, filed on Jul. 22, 2002.

(51) Int. Cl.
A61M 15/08    (2006.01)
A62B 7/00    (2006.01)

(52) U.S. Cl. ............... 128/207.18; 128/204.25; 128/204.18; 128/204.26; 128/207.13

(58) Field of Classification Search ........... 128/204.25, 128/200.24, 202.24, 204.18, 204.21, 204.22, 128/204.26, 205.11, 205.23, 205.24, 205.25, 128/206.22, 207.18
See application file for complete search history.

(56) References Cited

U.S. PATENT DOCUMENTS 3,581,742 A * 6/1971 Glenn ................. 128/204.19
4,718,870 A * 1/1988 Watts .................... 440/47
4,782,832 A   11/1988 Trimble et al.
5,036,847 A   8/1991 Labrune et al.
5,193,532 A * 3/1993 Moa et al. ............. 128/204.25
5,353,788 A * 10/1994 Miles .................... 128/204.23
5,636,630 A   6/1997 Caccavale et al.
5,752,510 A   5/1998 Goldstein
5,975,077 A * 11/1999 Hofstetter et al. ...... 128/204.24

(Continued)

FOREIGN PATENT DOCUMENTS

DE    10105383 A1 * 8/2002
FR    2733688        11/1996
WO    WO 02/062413 A2 * 8/2002

OTHER PUBLICATIONS

International Search Report dated Dec. 2, 2003 from PCT/IL2003/000599.

Primary Examiner—Justine R Yu
Assistant Examiner—Clinton Ostrup
(74) Attorney, Agent, or Firm—Ohlandt, Greeley, Ruggiero & Perle, L.L.P.

(57) ABSTRACT

A system and method are disclosed for the provision of assisted breathing by the delivery of a controlled pressurized airflow to the pulmonary airway of a user with breathing disorders. The system comprises a source of compressed respiratory gas (112), a user interface unit (115) including at least one Venturi device (120) and a thin flexible tubing (116) connecting between the source of high pressure gas (112) and the Venturi device. The system and method provide a regulated and controlled flow of air to the user (105) in accordance with the user needs. The invention further discloses a novel small light-weight user interface for replacing prior art breathing masks.

23 Claims, 9 Drawing Sheets

U.S. PATENT DOCUMENTS

| | | |
|---|---|---|
| 5,979,444 A | 11/1999 | Sherrod |
| 6,273,087 B1 * | 8/2001 | Boussignac et al. .... 128/204.22 |
| 6,363,935 B1 | 4/2002 | Boussignac |
| 6,561,188 B1 * | 5/2003 | Ellis ...................... 128/206.11 |
| 6,814,075 B2 * | 11/2004 | Boussignac ............ 128/204.24 |
| 7,080,645 B2 * | 7/2006 | Genger et al. .......... 128/204.18 |
| 2002/0096174 A1 * | 7/2002 | Hill et al. .................... 280/602 |
| 2006/0180149 A1 * | 8/2006 | Matarasso .............. 128/204.18 |

* cited by examiner

RESPIRATORY AID APPARATUS AND METHOD

RELATED APPLICATION

This application claims priority to International Application Number PCT/IL2003/000599 filed on Jul. 22, 2003, which claims priority to U.S. Provisional Patent Application Ser. No. 60/397,042, filed Jul. 22, 2002 the contents of which are incorporated herein by reference.

BACKGROUND OF THE INVENTION

1. Field of the Invention

The present invention generally relates to a respiratory aid for the alleviation of breathing and airway disorders, and more specifically to a respiratory aid comprising a Venturi air pump.

2. Discussion of the Related Art

The present invention relates to respiratory disorders in which external devices are used for delivering respiratory gas to assist spontaneous or forced breathing. Although the invention relates in particular to sleep apnea, the device and method disclosed in the following are not limited to this particular use and can be utilized for the alleviation of other respiratory disorders as well.

Sleep apnea is a disorder characterized by full or partial cessation of breathing during sleep. Apnea is defined as an interruption in breathing (air-flow into the lungs) for at least ten seconds, accompanied by a decrease in oxygen saturation. Hypopnea is a milder form in which there is a 50% decrease in air-flow for more than ten seconds. The number of incidents in which there is an interruption in breathing define the severity of the disorder. Patients suffering from sleep-associated apnea may have as many as 300-500 such interruptions in air-flow per night, each lasting 30-40 seconds. Obstructive Sleep Apnea (OSA) is the most common apneic disorder stemming from a mechanical obstruction in the upper respiratory airways during sleep. It is caused by recurrent blockage or narrowing of the airways during sleep and reduction in oxygen saturation.

Following the period of cessation of breathing, an abrupt, but brief, waking occurs caused by the urgent need for oxygen. This requirement is met by a single powerful inhalation, usually accompanied by a loud snore. Since this phenomenon occurs many times per night, it causes a fragmented, and unsatisfactory, sleep pattern. As a result of the frequent oxygen deprivations during the night, the patient will experience tiredness and lassitude during the daytime, sometimes resulting in uncontrolled sleep episodes during waking hours. The severity of the sleep apnea is usually expressed by the average number of complete or partial blockages per hour.

A significant number of sleep apnea patients have been found to suffer from enhanced cardiovascular morbidity. In addition, sleep apnea has been shown to be a risk factor for: systemic hypertension, pulmonary hypertension, ischemic heart disease, acute myocardial infraction, and brain infarction. The daytime sleepiness and tiredness, associated with the fragmented sleep pattern, expose these patients to additional dangers such as traffic accidents and work-associated accidents.

The present invention addresses other breathing disorders as well. These include: intensive care patients requiring assisted breathing, post-operative patients, asthmatic patients, patients with emphysema, patients with severe lateral sclerosis, patients with chronic heart failure, multiple sclerosis patients, and other breathing-associated disorders.

People with moderate to severe OSA are usually treated with CPAP (Continuous Positive Airway Pressure). The CPAP device is essentially an air pump connected by flexible tubing to a mask worn by the patient. This forced air flow, the pressure of which can be regulated depending on the severity of the apnea in each individual, keeps the airways from collapsing, thus preventing the interruptions which result in the apneic episodes. A typical CPAP system is illustrated in FIG. 1A. It comprises an air blower 1 which supplies a continuous flow of compressed air at relatively low pressure, usually in the range 2 to 20 mbar (20-200 mm $H_2O$). The air stream is forced through the flexible wide-bore (20-25 mm) tubing 2 to the mask assembly 3 placed on the patient's face and held in place by a head-encircling elastic straps 4. In order to keep a positive pressure inside the CPAP mask, the mask must have a peripheral seal. There exist a variety of CPAP masks varying from full-face masks covering both nose and mouth as mask 3 of FIG. 1A, through nasal masks which cover only the nose, and include nostril assemblies, as shown in FIG. 1B, in which the air is directly administrated to the nostrils. The nostril assembly of FIG. 1B is held by a curved plastic holder 6 affixed to the patient's head for supporting tubing 2. Tubing 2 terminates with a rigid short tube 7 connecting between tubing 2 and nostril piece 5 inserted into the patient's nostril.

The CPAP device has been proven to be successful in preventing breathing obstruction during sleep but it suffers from a number of drawbacks, associated mainly with discomfort to the user, as detailed in the following:

1. A CPAP apparatus is cumbersome to use because the mask and its straps are uncomfortable to wear. The mask assembly, together with the thick air pipe, limits the sleep positions of the patient and confines his/her ability to turn in their sleep. Since turning during sleep is an activity not controlled by the patient, the CPAP device itself may cause such discomfort as to wake the patient, and/or reduce the quality of sleep.
2. The apparatus requires connection to a power supply, which limits the mobility of the patient, and interferes with activities when an electrical outlet is unavailable (flights, camping, etc).
3. Since the device supplies a constant positive airflow through the mask, the user is forced to exhale at a pressure greater than the incoming flow of air in order to overcome the blower pressure. This is particularly true for a CPAP having a full-face mask, but also for situations with a nasal mask when the patient exhales through the nose. This necessity runs counter to the natural breathing rhythm during sleep, and requires adaptation.
4. When using the more common nasal mask, the patient is often forced to exhale through the mouth, resulting in dryness of the oral cavity during the night.
5. Since the air flows under relatively low pressure, it must be forwarded in large diameter pipes. If a smaller diameter pipe is used, it will decrease the air pressure intended for breathing and the apparatus will lose its efficiency.
6. When temporarily there is no need for the device, it is the practice to disconnect the device from the user due to the discomfort of wearing the mask and the restrictions to the user movements when connected to the device. When the need returns, the device has to be fitted again.

Thus, in spite of the undoubted benefit of CPAP devices in preventing apneic episodes, it was found that many patients tend to stop using the device after a period of time due to discomfort.

Accordingly, it is the general objective of the present invention to provide device and method that supply the necessary positive airflow to prevent airway collapse while overcoming the disadvantages of present CPAP devices.

In particular, it is one object of the invention to provide a respiratory aid apparatus that minimizes discomfort to the user, is light in weight, is mobile, and can be operated by batteries independently of electric current supply.

It is another object of the invention to provide a respiratory aid method and system that allow control of airflow according to the needs of the user and that allow regulating the airflow during the respiration cycle, making the breathing process more normal and comfortable.

Yet it is another object of the invention to provide a respiratory aid method and system that can be easily turned on or off and that when turned off allows for a normal breathing with no need to disconnect the user from the system.

Yet it is a further object of the invention to provide a respiratory aid system and method that not only delivers airflow to the user during inhalation phase but further provides active removal of air from the user airways during the exhalation phase.

A further object of the invention is to provide a respiratory aid apparatus that can be used with any currently available breathing mask, and is small, effective, easy to manufacture and is of low cost.

Yet a further object of the invention is to provide a novel user interface unit that can replace currently available breathing masks, and is small, flexible, can be easily adjusted to fit the user and is much more comfortable than currently available masks

SUMMARY OF THE INVENTION

In accordance with the above objectives, the present invention provides a respiratory aid system and method for providing a user with respiratory gas at a pressure which will keep the airways open for avoiding breathing difficulties due to mechanical obstruction and/or disease processes. The proposed system overcomes the drawbacks of prior art systems, minimizes discomfort to the user and allows for accurate regulation of the airflow administrated to the user airways.

A broad aspect of the invention is the use of a Venturi device, incorporated within a user interface unit in fluid communication with a user's airways, for administrating a controlled pressure of air to a user.

Another aspect of the invention is a respiratory aid apparatus for administrating a controlled flow of respiratory gas to a user's airways. The apparatus comprises a source of a high pressure respiratory gas; a user interface unit, including at least one Venturi device, located proximal to the user's air intake organs in fluid communication with the user's airways; and a low cross-section flexible tubing connecting between the source of high pressure respiratory gas and the user interface unit. The Venturi device comprises a hollow member, defining a central space open at both sides, and an inlet port opening into the central space. One end of the Venturi device is open to surrounding ambient air and the second open end is directed toward the user airways. The inlet port of the Venturi device is configured to direct compressed gas entering the central space toward the user airways. The source of the high pressure respiratory gas may be an air compressor or a gas cylinder containing a high pressure of air, oxygen enriched air or pure oxygen. In accordance with the invention, the source of high pressure respiratory gas is provided with a regulator for regulating the output pressure of said source. Preferably, the apparatus is further provided with at least one sensor for detecting the respiratory cycle of the user and with at least one controller interposed between the source of high pressure respiratory gas and the user interface unit for controlling the pressure of compressed gas entering the Venturi device. In accordance with one embodiment of the invention, the Venturi device may further comprise a second inlet port opening into said central space, configured to direct compressed gas entering the central space toward the end open to ambient air for assisting removal of air from the user's airways, and with a controllable valve for directing the compressed air alternately to the first inlet port during inhalation phase and to the second inlet port during exhalation phase. The apparatus may be used with any available breathing mask.

A further aspect of the invention is a gas delivery user interface unit of reduced size for enhancing the user's comfort, that can replace any prior art breathing interface. The user interface unit includes at least one Venturi device. In accordance with one embodiment, the user interface unit comprises two Venturi devices provided with a nasal adaptor to be inserted into a nostril of the user. The two Venturi devices may be mounted on a mouth piece or on a connecting member to be placed between the upper lip and the nose of the user wherein the thin tubing delivering the compressed gas into the user interface may serve as strapping means for strapping the unit to the head of the user.

A further aspect of the invention is a method for supplying a controlled pressure of respiratory gas to a user, the method comprising: delivering a high pressure respiratory gas via a thin tubing to a user interface in fluid communication with the user's airways, the user interface is having an inlet port connectable to said thin tubing; and accelerating the high pressure respiratory gas upon entering the user interface by means of a Venturi device located at the inlet port of the user interface, the Venturi device is configured to direct flow of compressed air toward the user's airways, the Venturi device is having an end open to surrounding ambient air; thereby pumping ambient air into the user interface. The method further comprises controlling the pressure of the high pressure respiratory gas delivered to the user interface. The method may further comprise stopping the delivery of high pressure respiratory gas during exhalation phase.

BRIEF DESCRIPTION OF THE DRAWINGS

The present invention will be understood and appreciated more fully from the following detailed description taken in conjunction with the drawings in which.

DETAILED DESCRIPTION OF PREFERRED EMBODIMENTS

The present invention provides system and method for the alleviation of disorders of airway block, which result in the subsequent reduction in oxygen saturation, and the attendant morbidity, by providing the necessary air pressure to overcome airway collapse. In particular, the device and method described herein are intended to overcome most of the disadvantages of present CPAP devices. However, the present invention can be used as a respiratory aid to treat not only sleep apnea patients but any patient requiring positive airway pressure for alleviation of breathing difficulties and airway blocks, both for assisting spontaneous patient respiration and with modifications, for forced artificial respiration.

The present invention replaces the conventional blower and large-diameter air pipe, employed in prior art CPAP systems, by a high-pressured compressor and an air-amplifier Venturi assembly. As such, the device is simple in design, light in weight, and causes minimal discomfort to the user. When used with a tank of high-pressured air instead of a compressor, the device can be operated by batteries, eliminating the need for external power line and imparting the device portability. Furthermore, the present system and method allows for controlling of the air pressure delivered to the user according to the real-time physiological needs of the user and can be operated intermittently to supply positive pressure only during the inhalation phase.

Other advantages of the invention will be realized from the following description.

Figure 1B:
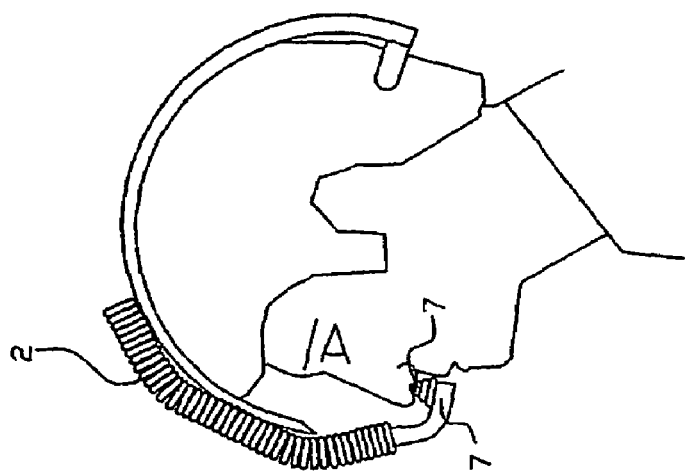
FIG. 1B is a schematic of illustration of another prior art CPAP mask.
Figure 1A:
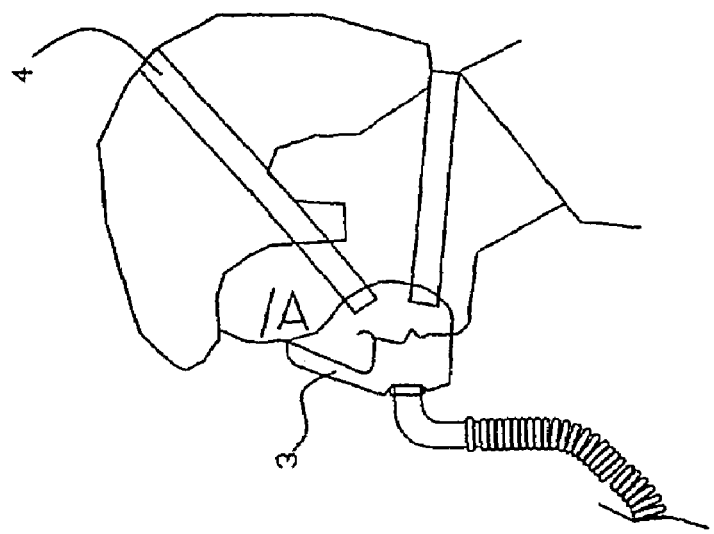
FIG. 1A is schematic illustration of a prior art CPAP apparatus and CPAP mask.
Figure 1A:
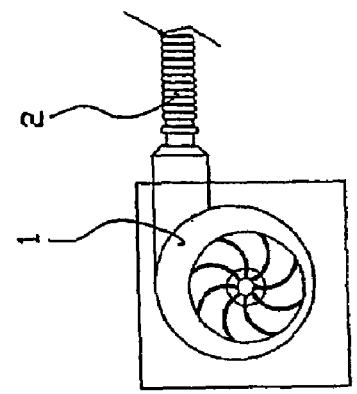
Figure 2:
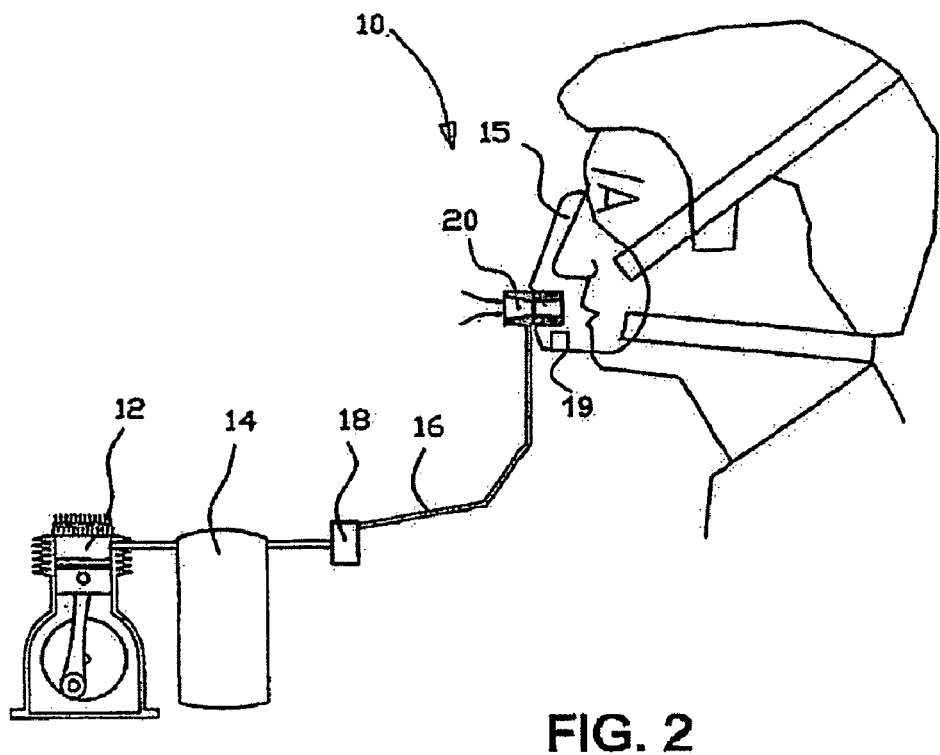
FIG. 2 is a schematic illustration of a respiratory system in accordance with the present invention combined with a prior art CPAP mask.

Referring now to FIG. 2, there is described a respiratory aid system, generally designated 10, in accordance with one embodiment of the present invention. Compressed air produced by compressor 12, flows through an optional pressure and/or humidifier 14. The air flows at high pressure of a few atmospheres through a thin flexible crush-resistant air tubing 16, preferably of 2-5 mm diameter. A fast-responding pressure valve 18 is located between tank 14 and tubing 16, regulating the air pressure delivered to the tubing. The compressed air enters mask 15 through a Venturi device 20 located at the inhalation port of the mask. The Venturi device 20, the principal operation of which is described below in association with FIG. 3, reduces the high-pressure delivered by the compressor to an acceptable desired low pressure value, preferably in the range of 2-20 mbar, while sucking air from its closest surroundings, i.e. from the mask vicinity, as indicated by the arrows. Venturi device 20, driven by the flow of high pressure air, functions as an air pump for both amplifying the volume and reducing the pressure of the air delivered to the user. Venturi device 20 is of very small dimensions (about 8-20 mm in diameter) and can be incorporated into all types of currently available breathing masks without further modifications, providing care is taken to form an air-tight seal between the external surface of the Venturi device and the inner surface of the inhalation port. In the embodiment shown here, Venturi device 20 is incorporated in the inhalation port of a conventional prior art face mask similar to the mask shown in FIG. 1.

Figure 3:
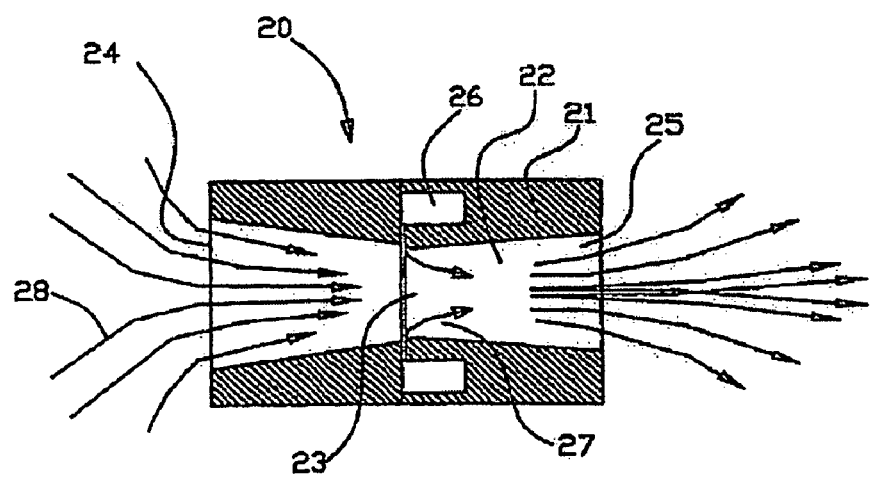
FIG. 3 is a schematic illustration demonstrating the operation of the Venturi device.

FIG. 3. is a schematic cross sectional view of Venturi device 20 demonstrating the operation of the Venturi device as an air pump. Venturi device 20 is an elongated tubular member 21 having a central space 22 open at both ends 24 and 25 and configured to have a throat portion 23. An annular compressed air chamber 26, having an inlet (not shown) for connecting to a tubing of compressed air, is in fluid communication with throat portion 23 of central space 22. The right corner of the junction between compressed air chamber 26 and central space 22 is rounded, directing air entering throat portion 23 from compressed-air chamber 26 to flow to the right as indicated by the arrows 27. When a flow of high pressure air from compressed air chamber 26 enters into the enlarged central space 22, a suction is created, due to the Venturi effect, entraining additional ambient air 28 from the surrounding space to be drawn into central space 22 through open end 24 toward open end 25. In accordance with the present invention, upstream open end 24 is in fluid communication with ambient air while downstream open end 25 is in fluid communication with the user airways via the inhalation port of mask 15. A particular construction of an embodiment of Venturi device 20 is described below in association with FIG. 6. It will be realized by a person skilled in the art that the Venturi device of the present invention is not limited to the particular construction described hereinabove and below and that other constructions can be used. Thus for example, it will be realized by persons skilled in the art that the throat portion 23 of central space 22 enhances the aerodynamics properties of Venturi 20 but that central space 22 may be of constant cross section.

Figure 4:
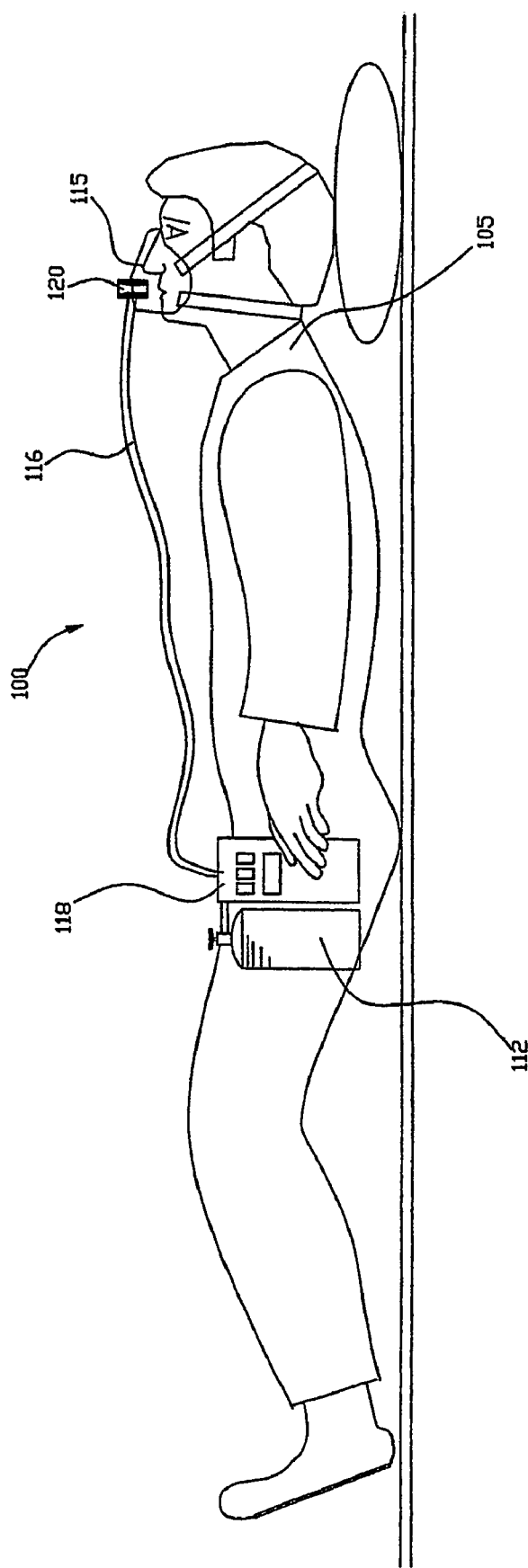
FIG. 4 is a schematic illustration of a portable respiratory system in accordance with the present invention.

Referring back to FIG. 2, in accordance with the embodiment described herein, the source of the high pressure air is compressor 12. Compressor 12 is preferably an oil-less compressor for avoiding oil fume contamination of the air delivered to the user. Preferably, compressor 12 is a quiet compressor, having controllable output pressure in the range of about 2-6 atmospheres. Examples for compressors that can be used with the present invention are vane air compressors such as model 0211 distributed by GAST, diaphragm air compressors such as Gast DOA models or piston air compressors such as Gast SOA models. A tank 14 can optionally be installed between compressor 12 and valve 18 for flattening the periodical amplitude of the compressor output pressure for obtaining a constant output pressure independent of the cyclic operation of the compressor. Tank 14 may further serve as a humidifying unit for regulating the humidity of the air delivered to the user. Alternatively, the source for high pressure air may be a portable tank containing high pressure air or other respiratory gas. For example, the high pressure respiratory gas may be air enriched with oxygen or can be pure oxygen. It will be realized that in accordance with the invention, the high pressure source serves mainly as the driving force for the system while most of the air delivered to the user is actually ambient air drawn from the surrounding. Thus, a high pressure tank of a moderate size can drive the system for a considerable period of time, rendering the whole apparatus mobile, and eliminating the need for external power lines. FIG. 4 illustrates such a mobile respiratory aid apparatus, generally designated 100, in use for assisting respiratory of patient 105. Portable apparatus 100 comprises a small container of compressed respiratory gas 112 connected by thin tubing 116 to user interface unit 115 via Venturi device 120. The apparatus may further comprise a controller 118 including a user interface for entering operation parameters and a controllable valve (not shown) for regulating the flow of gas administrated to the patient. Container 112 may contain compressed air, oxygen enriched air or pure oxygen. It will be realized that the weight and size of an apparatus such as shown in FIG. 4 is mainly determined by the dimensions of gas container 112, as the user interface unit 115 (which may be of reduced size as described below), thin tubing 116 and controller 118 can be easily packed into a package of insignificant volume and weight. In this respect the advantages of a small, light-weight portable respiratory apparatus which may be carried by emergency medical personnel on their body as part of the first-aid equipment, cannot be overestimated for civilian as well as for military applications. For example, it was found that in cases of head injuries and in particular traumatic brain injury (TBI), immediate ventilation to insure proper oxygen supply may positively affect respiratory cardiovascular function, increase survival rate, accelerate recovery and reduce long-term disabilities significantly, even in cases when injured person do not seem to lose his/her spontaneous breathing ability. An apparatus as of FIG. 4 can be used for immediate ventilation of the injured person at the scene of injury and during evacuation, until the injured person is brought to a medical facility. This is of particular importance, for example, in military situations where a first ventilation aid can be provided to an injured soldier by the medical personnel in the field. Likewise, apparatus as of FIG. 4 may be used by emergency medical staff arriving at accident scenes, or can be carried as part of the first aid equipment during activities in unpopulated areas, such as mountain climbing etc.

It will be realized that the apparatus described in FIG. 2 (or FIG. 4) can be used as is to replace prior art CPAP for providing continuous positive pressure to the user. However, the new features of the invention can be utilized for rendering the system to be far more advantageous as described in the following.

Due to the high pressure in tubing 16 a change of pressure at the entrance to tubing 16 immediately results in a corresponding change of the input pressure to Venturi device 20, unlike the prior art CPAP apparatus where the much lower pressure inside the wide-bore tubing requires a longer time for equalizing the pressure along the tubing. This allows for a simple real-time regulation of the airflow provided to the user by controlling the input pressure at the entrance to tubing 16. Regulation of the airflow in accordance with the user needs can be thus obtained by installing at least one sensor 19, for monitoring user breathing and connecting the sensor to a controller which controls the input pressure to tubing 16. The sensor may be any sensor known in the art for monitoring a breathing cycle. For example, sensor 19 may be incorporated in the user interface unit for monitoring changes induced by inhalation or exhalation. Sensor 19 may be a sound transducer for detecting breathing sounds, a sensitive pressure detector monitoring the drop of pressure at the commence of inhalation phases and increase of pressure at the commence exhalation phase by means of a sensitive diaphragm and the like, or a sensitive temperature for detecting temperature variation such as temperature increase at the nasal orifice during exhalation. Alternatively, the sensor may be a pneumatic or mechanical breathing belt attached to the user's chest for detecting expansion and contraction of the chest.

The control circuit allows for regulating the positive pressure in accordance with the user respiratory cycle such that air may be delivered only during inhalation phase, resulting in enhanced efficiency of the system and more importantly in greater ease and benefit to the user. The ability to compress air only during inhalation and to stop during exhalation considerably eases the operation of the system, especially for users in need of relatively high pressure to relieve the blockage of the pulmonary airway. Furthermore, the control circuit may include a programmable microprocessor including a memory device which monitors the user breathing pattern over time enabling a long term control of the airflow delivered to the user. Hence, during periods of normal non-obstructive breathing, the supply of positive pressure can be turned off completely, while upon detection of a breathing disorder, for example by detecting a cessation of breath or a significant change in the breath periodicity, the positive pressure is turned on. It must be emphasized that as soon as the flow of compressed gas into Venturi device 20 ceases, the pressure inside the Venturi immediately drops to atmospheric pressure so that the Venturi device functions as a passive open tube of relatively large opening that does not inflict any resistance to normal breathing. This is noteworthy in particular with regard to the ease of exhalation.

In accordance with the invention, the input pressure at the entrance of tubing 16, and consequently the positive pressure delivered to the user, can be controlled, by a number of ways. In accordance with one method, the pressure is controlled by directly connecting the control circuit to compressor 12 for regulating the input power and consequently the operation speed and output pressure of the compressor. According to another, more preferable method, the output pressure of compressor 12 (flattened by optional tank 14) is kept constant and the pressure is controlled by means of pneumatic valve 18. It will be realized that a combination of the two methods is also possible. Pneumatic valve 18 may be an on/off valve, such as a solenoid actuated valve, or a continuous controllable operating valve, such as flow regulation valve. Where valve 18 is an on/off valve, regulation of the pressure can be obtained in the simplest way by keeping the valve open during inhalation phase and shut during exhalation phase. In such a case, an additional buffering tank may be installed between valve 18 and tubing 16 for allowing gradual build up of pressure during the inhalation phase and gradual drop of pressure during exhalation. Preferably, the high pressured respiratory gas is delivered to tubing 16 via valve 18 in a pulsating manner to allow controlling the average pressure delivered to tubing 16 by changing the frequency and duration of pulses. This allows for changing the amplitude of positive pressure supplied to the user in a continuous manner.

Figure 5:
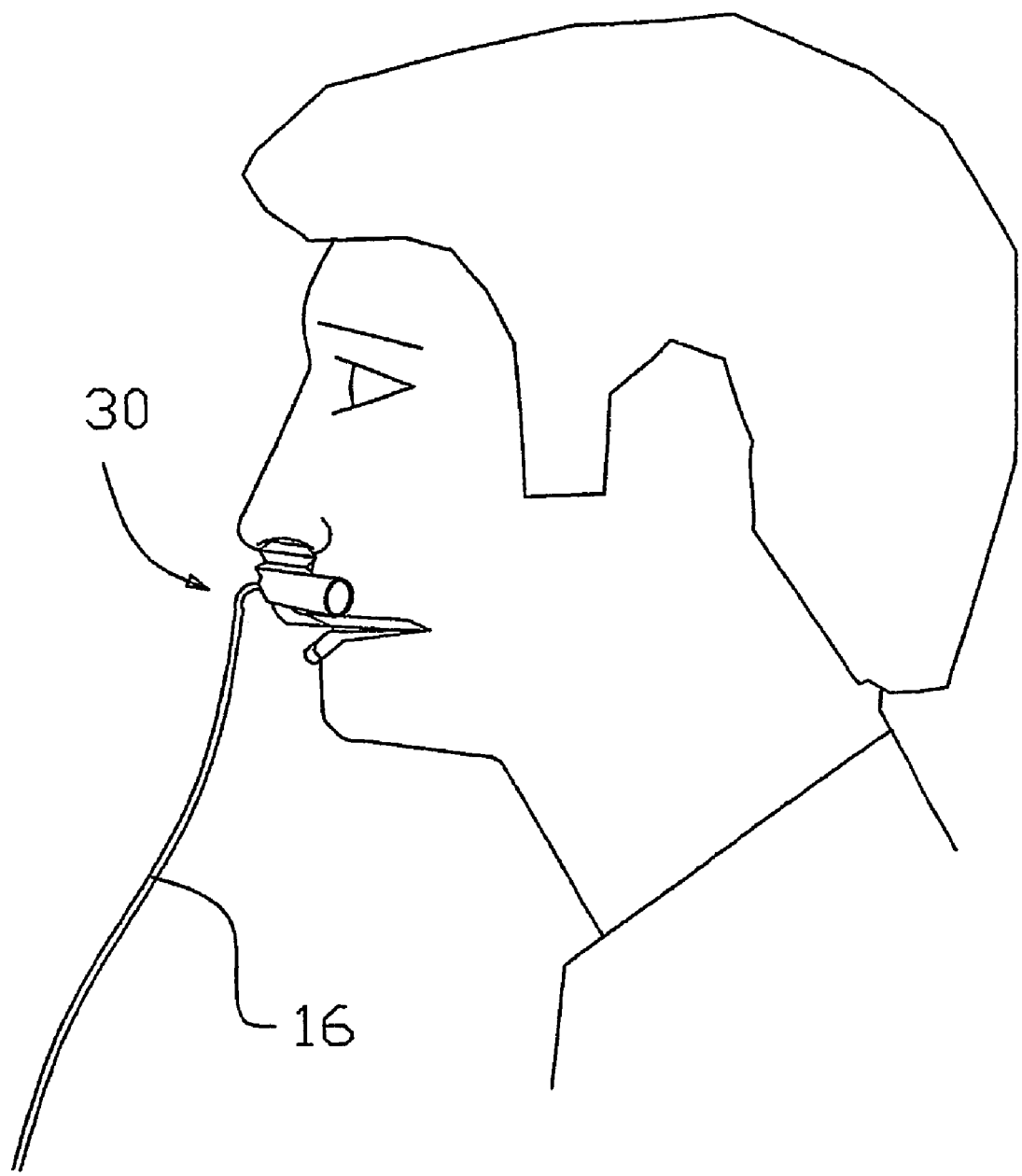
FIG. 5 is an illustration of the a novel user interface unit in accordance with one embodiment of the present invention.
Figure 5A:
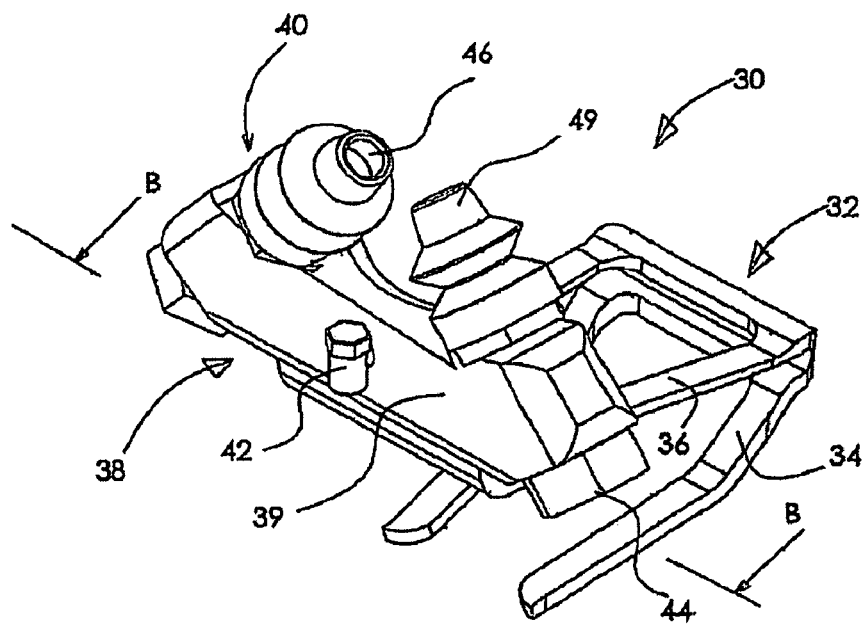
FIG. 5A is a perspective frontal view of the user interface unit of FIG. 5.
Figures 5B, 5C:
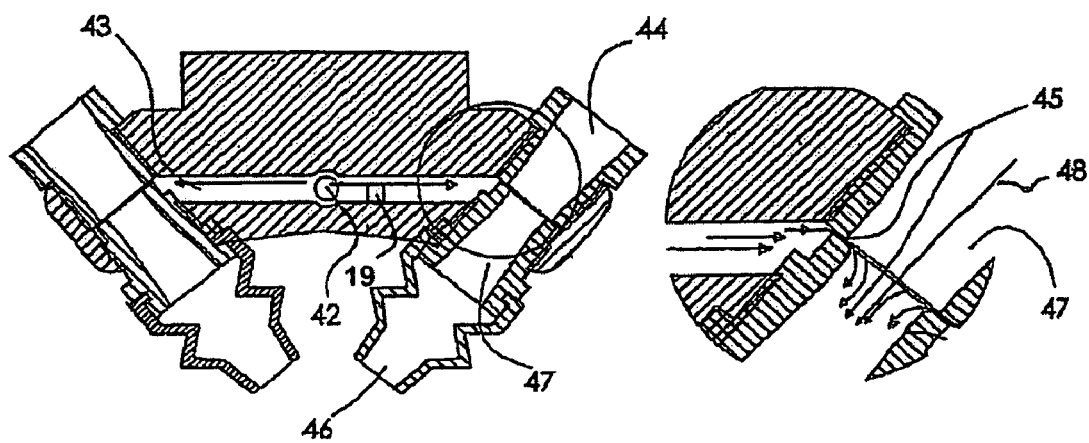
FIG. 5B is a cross sectional view along line B-B of FIG. 5A.
FIG. 5C is an exploded view of the encircled area of FIG. 5B.

The use of a thin and very light tubing for the flow of the compressed air, instead of the prior art wide-bore tubing, allows the replacement of conventional CPAP masks by an air delivery user interface of reduced size for enhancing the user comfort and providing a more aesthetic look. FIG. 5 depicts such a novel air delivery user interface unit in accordance with one embodiment of the invention that utilizes the mouth and jaw structure to support the small-sized unit and does not require head straps. The air delivery assembly, generally designated 30, is situated between the lower jaw and the nose and is dimensioned to protrude no further than the nose bridge. The device does not require a rigid jaw closure, therefore allowing the user to close and open his mouth during sleep. Assembly 30, shown in detail in FIG. 5A, includes a mouth piece 32, comprising two resilient arms 34 to be inserted into the mouth of the user under the upper teeth, or embracing the upper gums, connected to two resilient arms 36 on which the air delivering unit 38 is mounted such that frontal surface 39 of unit 38 is lying between nose and upper lip. Mouth-piece 32 is configured to allow the user to freely open and close his/her mouth. Unit 38 includes two Venturi devices 40 in fluid communication with high pressure inlet 42, as best seen in FIG. 5B and FIG. 5C, terminating with small conical bellows 49 to be inserted into the user's nostrils. In FIGS. 5A, 5B ad 5C, like numbers refer to like parts. In operation, high pressure respiratory gas is forced through inlet 42 to flow through common passage 43 toward Venturi devices 40. The airflow enters the central space 47 of each of Venturi devices 40 through narrow passage 45 thereby drawing ambient air from opening 44 to flow toward opening 46 as indicated by arrows 48, and into the user airways.

Figure 6A:
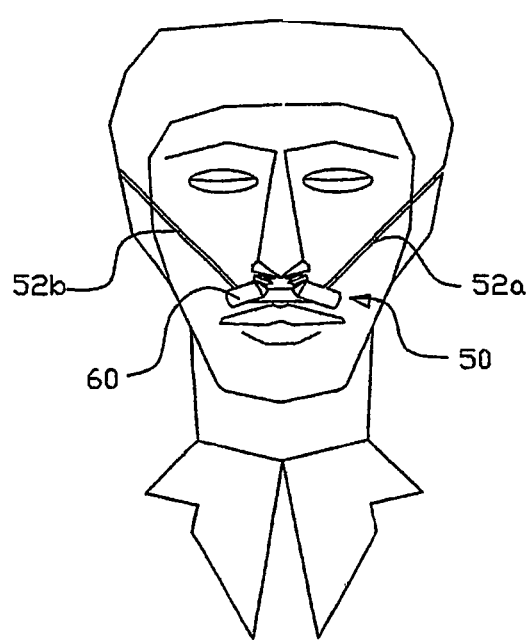
FIGS. 6A-6C are frontal, profile and rear views, respectively, of an air delivering user interface unit in accordance with another embodiment of the invention.
Figure 6B:
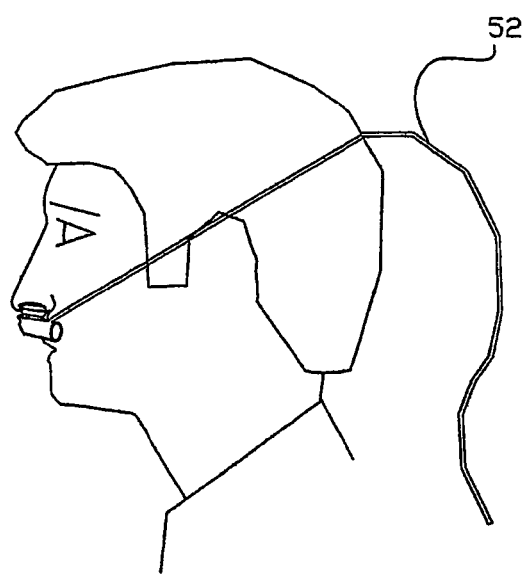
Figure 6C:
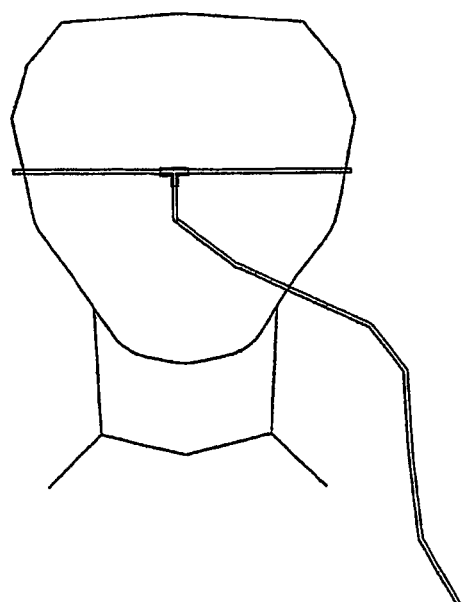
Figure 7A:
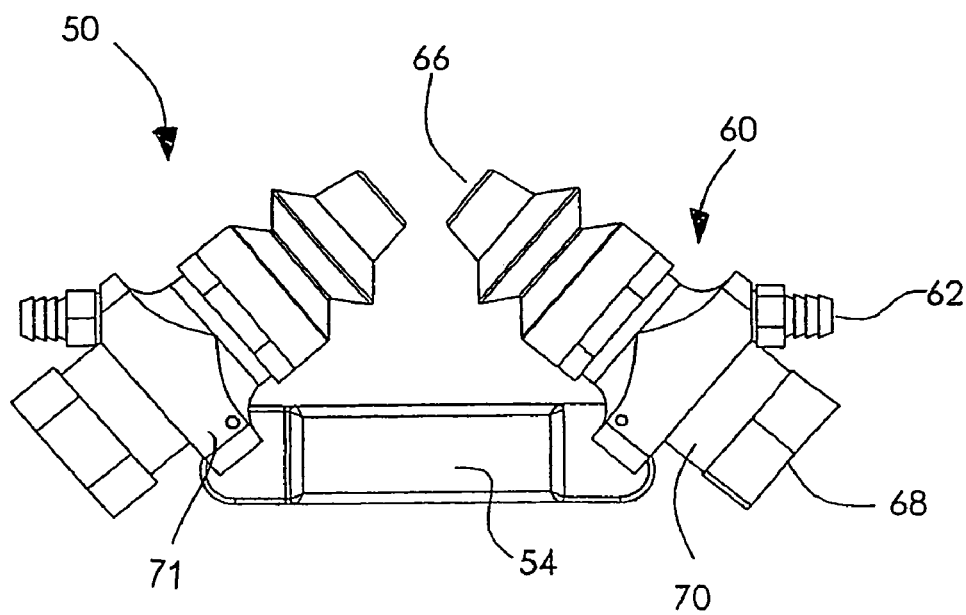
FIGS. 7A and 7B are a perspective view and exploded view, respectively, of the Venturi assembly of FIG. 6.
Figure 7B:
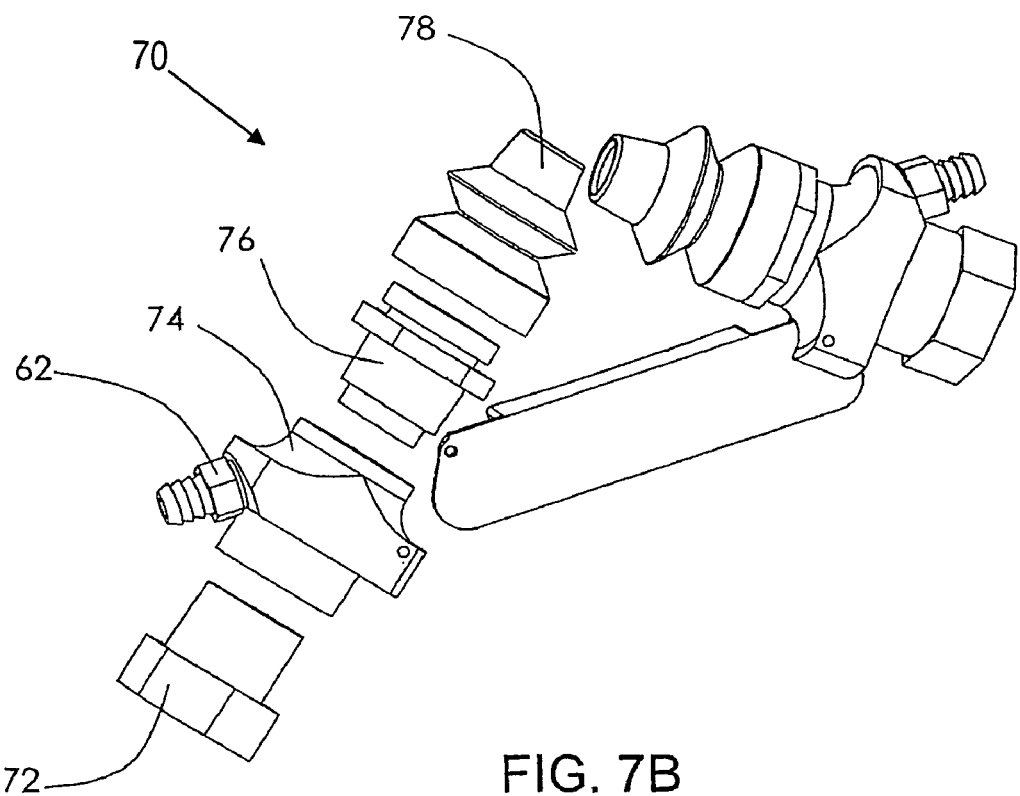
Figure 7C:
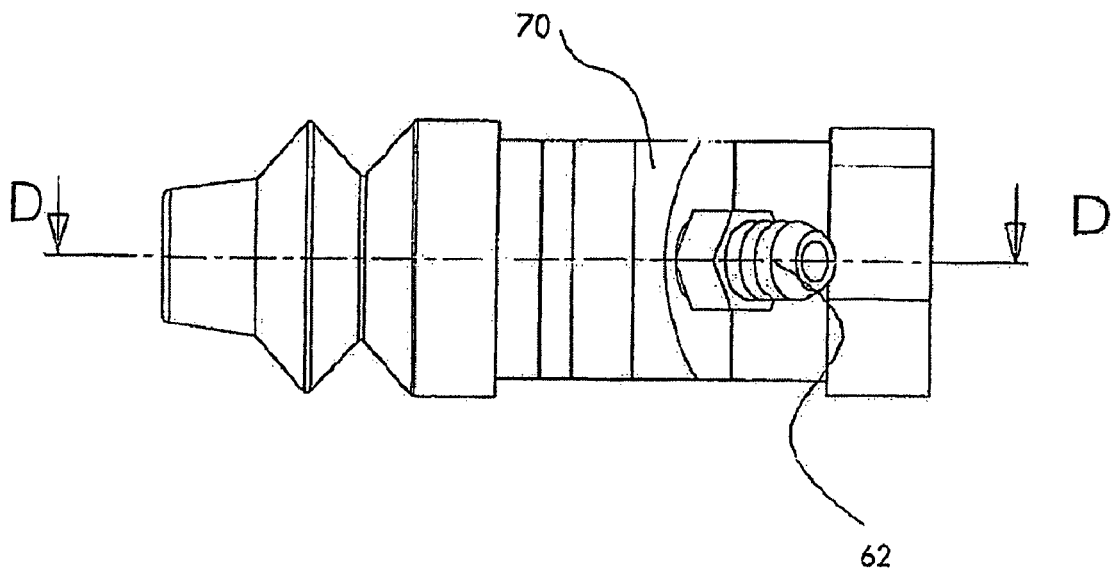
FIG. 7C is a side view of the Venturi assembly of FIG. 7A.
Figure 7D:
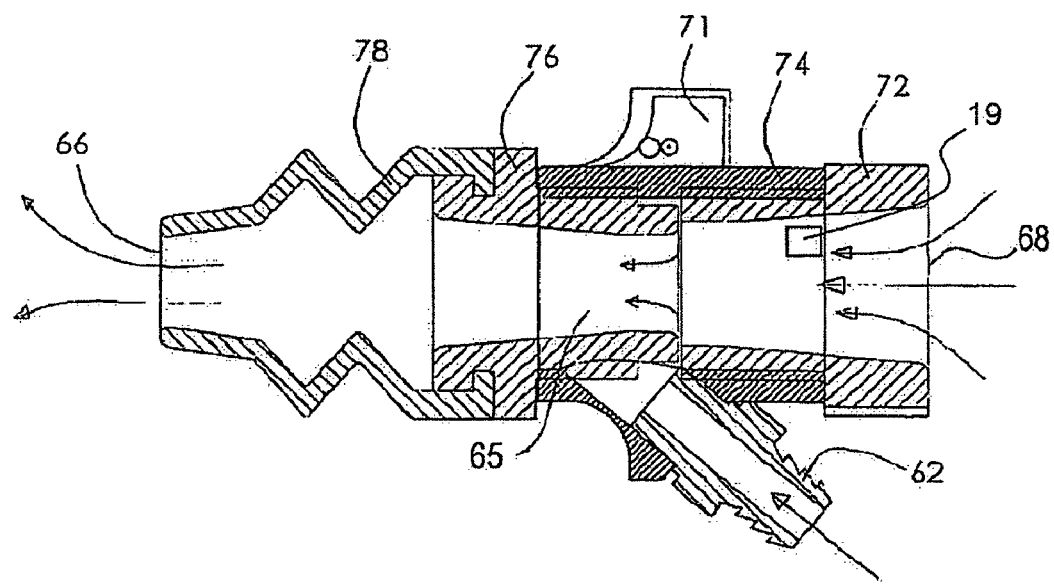
FIG. 7D is a cross section along line D-D of FIG. 7C.

Another embodiment of a novel user interface unit is depicted in FIGS. 6 and 7. In accordance with this embodiment, tubing 52 delivering the air to user interface unit 50 serves also as the means for holding device 50 in place. As can be seen, tubing 52 bifurcates via a T-connector into two branches 52a and 52b, each delivering air to corresponding nasal extension 55 via corresponding Venturi 60. Alternatively, or additionally, tubes 52a and 52b may be each wrapped to form a loop around one of the user's ears for enhancing the grip between unit 50 and the user's head and for keeping unit 50 in place. Tubing 52 is made of crush-resistant material for preventing occlusion of the air pathway when pressure is applied on the tube such as for example by the head or trunk of the user. Tubing 52 may be flat, comprised for example from a ribbon of parallel tubes of small diameter aligned side by side, for enhancing the user's comfort.

User interface unit 50 of FIG. 6 is shown in detail in FIG. 7. User interface unit 50 comprises a flat elongated connector member 54 made of flexible material to be placed between mouth and nose and two Venturi devices 60 pivotally mounted by means of wings 71 on both sides thereof for allowing adjusting distance and angle for best fitting the user anatomy. Each of Venturi devices 60 is provided with an inlet 62 for connecting to tubing 52 delivering the high-pressure gas. Compressed air entering central space 65 through inlet 62 is directed to flow to the left toward opening 66. The upstream end 68 is open to the surrounding ambient air. As best seen in exploded view in FIG. 7B, main tube 70 comprises an upstream member 72, a central member 74, a downstream member 76 and a nasal extension 78 to be inserted into the user nostrils. The different parts are configured such that when assembled together a narrow annular gap is formed between parts 72 and 76 to allow flow of air from inlet 62 into central space 65. It will be realized that the constitution of Venturi 50 is not limited to the particular elements as described in FIG. 7B. Thus, the whole Venturi assembly may be fabricated as a one piece or a one or more components may be combined to form one integral part.

It will be appreciated that the combined use of the airflowing system as described in association with FIGS. 2 and 4 together with the proposed new interface unit as described in association with FIGS. 5 through 7, allows for the possibility to twist and turn during sleep without waking and without interfering with the operation of the system, thus significantly minimizing user's discomfort and improving sleep pattern.

Yet, in accordance with a further embodiment of the present invention, the high pressured airflow is utilized not only as the driving force for delivering air into the user's airway during inhalation but also as the driving force for assisting removal of air from the user airway during exhalation.

Figure 8A:
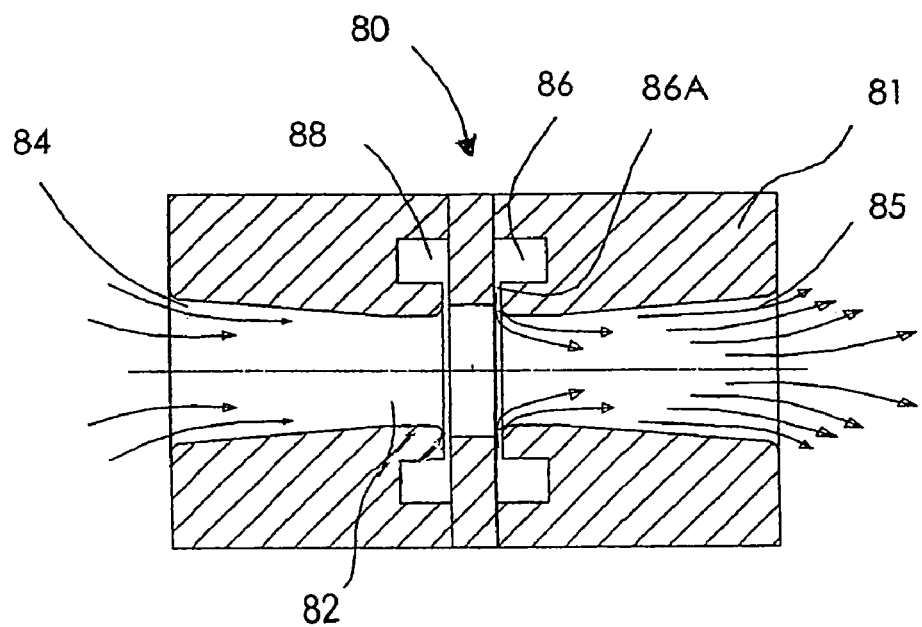
FIG. 8A and FIG. 8B are schematic illustrations of a bi-directional Venturi device demonstrating air flow during inhalation and exhalation, respectively.
Figure 8B:
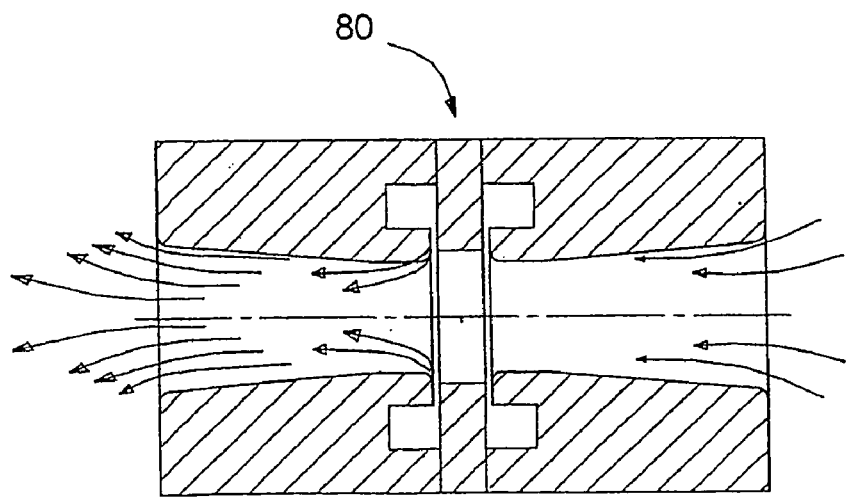

FIGS. 8A and 8B are schematic cross sectional views of a bi-directional Venturi assembly, generally designated 80, in accordance with a bi-directional embodiment of the invention, demonstrating the operation of the Venturi as a bi-directional air pump. Venturi assembly 80 is an elongated tubular member 81 having a central space 82 open at both ends 84 and 85. Two annular compressed air chambers 86 and 88 having an inlet (not shown) for connecting to a source of compressed air are in fluid communication with the central portion of central space 82 through narrow passages 86a and 88a, respectively. The junctions between passages 86a and 88a with central space 82 are configured such as to direct compressed air entering from chamber 86 to the right and to direct compressed air entering from chamber 88 to the left. In operation, compressed air is entering central space 82 alternately from chamber 86 to entrain ambient air to flow to the right as indicated by the arrows in FIG. 8A and from chamber 88 to entrain ambient air to flow to the left as indicated by the arrows in FIG. 8B. Thus, by using a simple valve which directs the compressed air alternately between chambers 86 and 88, the device can be once actuated for forwarding airflow into the user airways for the purpose of inhalation as described above, and then to reverse the airflow direction for supporting exhalation, hence to significantly relieve patients with breathing problems. Furthermore, the possibility to use a bi-directional air passage system and activate it to either compress and force air forward during inhalation, or remove air during exhalation, actually transforms the system into a respirator breathing unit facilitating forced breathing.

It will be realized that although the schematic description of FIG. 8 illustrates bi-directional Venturi assembly 80 to be symmetrical in respect to its left and right portions, in reality the Venturi assembly can be configured to have two asymmetric portions for allowing different forced to entrained ratios. Additionally, by regulating the pressure of forced gas into the Venturi assembly, as described above, it is possible to accurately regulate both forward and reverse airflow for best fitting the patient needs.

Although the invention has been described in conjunction with specific embodiments thereof, it is evident that many alternatives, modifications, and variations will be apparent to those skilled in the art. Accordingly, it will be appreciated by persons skilled in the art that the present invention is not limited to what has been particularly shown and described hereinabove. Rather the scope of the present invention is defined only by the claims which follow.

The invention claimed is:

1. A portable respiratory aid system for administrating a regulated flow of air to a person suffering from sleep apnea, the respiratory aid system comprising:

a source of high pressure air;

an air delivery nasal interface comprising two air delivery units configured for delivering a flow of air each to a respective nostril of said person, the two air delivery units being pivotally mounted on opposite ends of a flat elongated flexible member configured to be placed above the upper lip of said person, wherein each of said two air delivery units comprises a Venturi device, said Venturi device comprising a hollow member defining a central space and an inlet which opens into said central space, a first open end opens to surrounding ambient air and a second open end being provided with a nasal adaptor attachable to a nostril of said person, wherein said first inlet is configured for receiving a flow of high pressure air via a thin flexible tubing and for directing said flow of high pressure air toward said second open end; and a thin flexible tubing bifurcating into two branches for delivering a flow of high pressure air from said source of high pressure air to said inlet of each Venturi device, said tubing being configured for serving as strapping means for strapping said air delivery nasal interface to said person's head;

at least one sensor for monitoring breathing of said person; and a control unit operably connected to said at least one sensor for regulating said flow of high pressure air in accordance with said monitored breathing, the control unit comprising a microprocessor and a memory device configured for monitoring a breathing pattern over time, thereby enabling a real-time regulation of said flow of air in accordance with respiratory cycles of said person and a long term regulation in accordance with said monitored breathing pattern.

2. The respiratory aid system of claim 1 wherein the thin tubing diameter is in the range of 2 to 5 mm and wherein said source of high pressure air has an output pressure in the range of 2 to 6 Atmospheres.

3. The respiratory aid system of claim 1 wherein said source of high pressure air is a portable container of compressed air.

4. The respiratory aid system of claim 1 wherein said source of high pressure air is an oil-less air compressor.

5. The respiratory aid system of claim 4 wherein said control unit is operably connected to said oil-less compressor.

6. The respiratory aid system of claim 1 wherein said at least one sensor is a sound transducer or a temperature detector.

7. The respiratory aid system of claim 1 wherein said at least one sensor is a pressure detector.

8. The respiratory aid system of claim 1 further comprising a controllable valve operably connected to said control unit, said controllable valve is interposed between said source of high pressure air and said first inlet of the at least one Venturi device.

9. The respiratory aid system of claim 8 wherein said controllable valve is an on/off valve.

10. The respiratory aid system of claim 8 wherein said controllable valve is a flow regulation valve.

11. The respiratory aid system of claim 1 further comprising a chest-mounted sensor adapted for detecting expansion and contraction of the chest of the person.

12. The respiratory aid system of claim 1 wherein at least one of said Venturi device further comprises a second inlet which opens into said central space and wherein said second inlet is configured for receiving a flow of high pressure air and for directing said flow of high pressure air toward said first open end.

13. The respiratory air system of claim 1 wherein said long term regulation in accordance with said monitored breathing pattern comprises turning on said flow of high pressure air upon detection of a breathing disorder and turning it off upon detection of a regular non-obstructive breathing.

14. An air delivery nasal interface comprising:
two air delivery units configured for delivering a flow of air to one of a pair of nostrils of a person, said two air delivery units being pivotally mounted on opposite ends of a flat elongated flexible member configured to be placed above the upper lip of said person, wherein each of said two air delivery units comprises a Venturi device, wherein each of said Venturi devices comprises a hollow chamber defining a central space, and an inlet which opens into said central space, said hollow member having a first open end which opens to surrounding ambient air and a second open end provided with a nasal adaptor, wherein the inlet of each of said Venturi devices is configured to receive a flow of high pressure air via a thin tubing and to direct said flow of high pressure air toward said second open end, wherein said flow of high pressure air upon entering said central space acts as a driving force for drawing ambient air through said first end toward said second open end;
a thin flexible tubing bifurcating into two branches for connecting a source of high pressure air to each of said inlets of said two air delivery units, said tubing being configured for serving as strapping means for strapping said air delivery nasal interface to a person's head; and
at least one sensor for monitoring breathing of a person using the air delivery nasal interface.

15. The air delivery nasal interface of claim 14 wherein said at least one sensor is a sound transducer or a temperature detector.

16. The air delivery nasal interface of claim 14 wherein said at least one sensor is a pressure detector.

17. The air delivery nasal interface of claim 14 further comprising a controllable valve interposed upstream of the two first inlets of said two air delivering units.

18. The air delivery nasal interface of claim 14 wherein the at least one Venturi devices further comprises a second inlet which opens into said central space and wherein said second inlet is configured for receiving a flow of high pressure air and to direct said flow of high pressure air toward said first open end.

19. The air delivery nasal interface of claim 18 further comprising a controllable valve operably interposed between said first and second inlets, the controllable valve is configured for allowing direction of flow to either the first inlet or to the second inlet.

20. A method for administrating a controlled flow of air to a person suffering from sleep apnea, in accordance with the real-time needs of said person, the method comprising: connecting a portable source of high pressure air by means of a thin tubing to an air delivery nasal interface wherein the air delivery nasal interface comprises two air delivery units configured for delivering a flow of air each to a respective nostril of said person, the two air delivery units being pivotally mounted on opposite ends of a flat elongated flexible member configured to be placed above the upper lip of said person, wherein each of said two air delivery units comprises a Venturi device, both Venturi devices, comprising a hollow member defining a central space, an inlet that opens into said central space, each hollow member having a first open end that opens into surrounding ambient air and a second open end provided with a nasal adaptor attachable to a person's nostril, each of said Venturi devices being configured to receive a flow of high pressure air through said inlet and to direct said flow of high pressure air toward said second end, thereby drawing ambient air from said first open end toward said second open end and reducing said high pressure to a pressure of lower value; monitoring the breathing of said person by means of a sensor; and delivering a flow of high pressure air from said source of high pressure air via said thin tubing to said air delivery nasal interface via the inlets of said Venturi devices; and automatically regulating said flow of high pressure air in accordance with the monitored breathing so as to administer a flow of a desired pressure to said person when an apneic breathing pattern is detected and turning off the flow of high pressure air upon detection of a regular non-obstructed breathing.

21. The method of claim 20 wherein said source of high pressure air is a container of high pressure air.

22. The method of claim 20 wherein said source of high pressure air is an oil-less air compressor.

23. The method of claim 20, wherein said regulating the flow of air in accordance with the monitored breathing comprises the steps of:
automatically turning off the flow of high pressure during exhalation phase; and
automatically turning on the flow of high pressure air during inhalation phase.

* * * * *